United States Patent
Klofta et al.

(10) Patent No.: US 9,956,312 B2
(45) Date of Patent: May 1, 2018

(54) ABSORBENT ARTICLES COMPRISING WETNESS INDICATORS

(75) Inventors: Thomas James Klofta, Cincinnati, OH (US); Ryan Louis Malsch, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 2100 days.

(21) Appl. No.: 12/960,587

(22) Filed: Dec. 6, 2010

(65) Prior Publication Data

US 2011/0137274 A1 Jun. 9, 2011

(51) Int. Cl.
*A61F 13/42* (2006.01)
*A61L 15/56* (2006.01)

(52) U.S. Cl.
CPC .............. *A61L 15/56* (2013.01); *A61F 13/42* (2013.01); *A61F 2013/422* (2013.01); *A61F 2013/426* (2013.01); *A61F 2013/427* (2013.01)

(58) Field of Classification Search
CPC .................. A61F 13/42; A61F 13/8405; A61F 2013/422; A61F 2013/426; A61F 2013/429; A61F 2013/8447; A61F 2013/845
USPC ........................................................ 604/361
See application file for complete search history.

(56) References Cited

U.S. PATENT DOCUMENTS

| | | | | |
|---|---|---|---|---|
| 4,931,051 A * | 6/1990 | Castello | ........................ | 604/361 |
| 6,933,421 B2 * | 8/2005 | Topolkaraev et al. | ........ | 604/361 |
| 7,159,532 B2 * | 1/2007 | Klofta et al. | ................. | 116/206 |
| 8,061,292 B2 * | 11/2011 | Ahmed et al. | ................ | 116/206 |
| 8,129,582 B2 * | 3/2012 | Jackson et al. | ............... | 604/361 |
| 8,497,409 B2 * | 7/2013 | Mosbacher et al. | .......... | 604/361 |
| 2003/0164136 A1 | 9/2003 | Klofta et al. | | |
| 2005/0199177 A1 | 9/2005 | Klofta et al. | | |
| 2005/0256492 A1 | 11/2005 | Yamakawa et al. | | |
| 2007/0032766 A1 * | 2/2007 | Liu et al. | ...................... | 604/361 |
| 2008/0234644 A1 * | 9/2008 | Hansson et al. | ............. | 604/360 |
| 2008/0312625 A1 | 12/2008 | Hundorf et al. | | |
| 2010/0004613 A1 * | 1/2010 | Cohen | .......................... | 604/361 |
| 2010/0262100 A1 * | 10/2010 | Klofta | .......................... | 604/361 |

FOREIGN PATENT DOCUMENTS

| | | |
|---|---|---|
| JP | 2009-250642 A | 10/2009 |
| WO | WO 2001/41691 | 6/2001 |
| WO | WO 2010/120706 A1 | 10/2010 |

OTHER PUBLICATIONS

International Search Report, PCT/US2010/059070, dated Mar. 21, 2011, 13 pages.

* cited by examiner

*Primary Examiner* — Lynne Anderson
(74) *Attorney, Agent, or Firm* — James T. Fondriest; Kathleen Y. Carter

(57) ABSTRACT

An absorbent article that includes a backsheet, a wetness indicator composition having good stability, and an absorbent core. The wetness indicator composition includes a stabilizer, a colorant, and a matrix. The colorant has first and second color states associated with first and second wetness indicator states. The wetness indicator exhibits no color change after 10 days when measured according to the CTH Stability Test.

19 Claims, 2 Drawing Sheets

ABSORBENT ARTICLES COMPRISING WETNESS INDICATORS

CROSS REFERENCE TO RELATED APPLICATION

This application claims the benefit of U.S. Provisional Application No. 61/267,225, filed on Dec. 7, 2009.

FIELD OF THE INVENTION

This invention is directed to absorbent articles comprising wetness indicator compositions. Particularly, wetness indication compositions having improved colorant stability.

BACKGROUND OF THE INVENTION

Absorbent articles that include a wetness indicator are known. In some instances, the wetness indicator may include a colorant adapted to change in appearance, i.e., appear, disappear, change color, etc., upon contact with liquids such as, urine, runny bowel movements, menses, etc., in the article. Wetness indicators may be of the substantially insoluble type (i.e, they are designed to generally remains in the same location of the article before and after being wetted with liquid). Some wetness indicator compositions may be designed to simply disappear into the core of the diaper after being wetted (e.g., wetted with urine). Wetness indicator compositions typically function to serve at least one of the following: 1) the wetness indicator composition should effectively adhere, but not substantially bleed through, to the substrate on which it is applied (e.g., the backsheet) and should possess an optimum balance of cohesive strength and flexibility to remain intact during storage, as well as upon and after being wetted, 2) the initial color of the wetness indicator composition should not prematurely change color such that it confuses the caregiver or wearer as to whether a wetness event has occurred, 3) the color change of the wetness indicator composition should occur as quickly as possible after the wetness event, 4) the contrast in colors between the dry and wetted states of the wetness indicator composition should be great enough to signal the occurrence of the wetness event, 5) the color signaling the wetness event should remain visible for a long period of time after the wetness event and should not migrate to other regions of the diaper such that the signal denoting the wetness event becomes difficult or impossible to interpret, 6) the wetness indicators of the present invention should adhere, but not substantially bleed through, to the substrate that it comes in direct contact with (e.g., the nonwoven dusting layer) or that it is in close proximity to (e.g., the core cover) to provide for adequate wicking of fluid (e.g., urine), 7) the wetness indicator composition should remain stable (i.e., not change color prior to a wetness event) when placed in close proximity (if not direct contact) with higher (versus the colorant of the wetness indicator composition) pH absorbent article components, and 8) the wetness indicator composition should be easily made, easily processed for application onto the wearable article, be safe, and of economical cost.

While problems realized in the past (including high humidity and temperature environments) remain, there are additional challenges associated with new diaper designs, particularly including diaper designs comprising absorbent cores that are substantially cellulose free. These core designs comprise increased levels of absorbent polymer material (sometimes referred to as superabsorbent polymer or absorbent gelling material), adhesives (including, thermoplastic adhesive materials), and surfactants. Each of these comprise chemical compositions that can alter the pH of the wetness indicator composition and thus cause a color change prior to a wetness event. Particularly, alkaline surfactants containing amine, amide, or quaternary functionalities are especially problematic for wetness indicators comprising colorants that change color as the pH rises; but even lower pH moieties like carboxylates can also pose challenges and prematurely activate certain colorants within such wetness indicator compositions.

One color changing colorant active used in at least some wetness indicators is a pH indicator such as bromocresol green or the like, which changes color from yellow to blue in the pH range of 3.8 to 5.4. To maintain the yellow color of bromocresol green in a dry state, the wetness indicator composition may need to be relatively acidic. A wetness indicator that contains the bromocresol green pH indicator colorant typically remains yellow until it is contacted with a fluid such as urine. Upon contact with a liquid such as urine, the bromocresol green pH indicator colorant indicator will turn blue to indicate the presence of the liquid, due to the higher pH of the urine. In wetness indicator compositions that include a pH activated colorant, it may be desirable to incorporate acids (as well as other chemical components discussed in more detail below) in the wetness indicator composition to stabilize the wetness indicator (i.e., prevent an undesired color change of the pH indicators prior to a wetness event).

Placing the wetness indicator composition in close proximity to the absorbent core of a diaper, which is substantially cellulose free or includes a relatively high level of surfactant, may cause a premature color change in the colorant. This may be especially true when the diaper design utilizes lower basis weight and more breathable substrates (e.g., backsheets, dusting layers, and core covers) because these substrates may allow pH altering chemicals to come in closer proximity with the wetness indicator composition. Thus, it may be desirable to optimize the acid content of the wetness indicator composition relative to any other materials present in the composition to aid in preventing premature color change. But, while the acid content is optimized for stability, it may also be desirable to optimize the wetness indicator composition for proper functioning of the other properties (e.g., kinetics, dye retention, stability, adhesion). If too much acid or too strong of an acid mixture is incorporated, the pH can remain suppressed even after the wetness event such that the yellow color of the bromocresol green, for instance, persists and no blue color (signaling a wetness event) results even when a wetness event has occurred. If too little acid or too weak of an acid mixture is incorporated, the wetness indicator composition can prematurely change color. Thus, the acid content should be optimized so the wetness indicator composition remains stable under various storage scenarios, as well as within new absorbent article designs.

Beyond these stability issues, it may be desirable to configure the wetness indicator composition so that it contacts or even adheres to an inner adjacent layer of substrate (e.g., the dusting layer if the wetness indicator is disposed on the backsheet) to facilitate wicking of fluid (e.g., urine) to the wetness indicator composition after a wetness event occurs. That is, when a gap exists between the wetness indicator composition and the inner adjacent substrate (e.g., the dusting layer), fluid may not travel from the absorbent core to the wetness indicator within the desired time to signal a wetness event. It may additionally be desired that there is substantial contact/adherence of the wetness indicator to an inner adjacent substrate to ensure that the wetness indicator composition is evenly (top to bottom and side to side) wetted and thus provides the full signal intended. This can be accomplished by providing a wetness indicator composition that has an optimized "open time" during its incorporation into an absorbent article (e.g., the wetness indicator may be applied as a hot melt adhesive that is in a molten state long enough to adhere to the substrate, but not so long that it bleeds through the substrate or to other materials that could negatively impact the stability of the colorant). An ideal open time is long enough to allow efficient coating of the backsheet film but short enough so fast solidification of the wetness indicator prevents bleeding into regions that could negatively impact the stability of the colorant.

Accordingly, it would be desirable to provide a wetness indicator that is stable in the absorbent core of a disposable absorbent article. It would also be desirable to provide a wetness indicator that has a suitable open time for use in absorbent articles comprising lower basis weight and breathable films and nonwovens. It would further be desirable to provide a wetness indicator that has suitable color change kinetics.

SUMMARY OF THE INVENTION

In order to provide a solution to the problems set forth above, at least one embodiment disclosed herein is an absorbent article comprising an absorbent core and a backsheet. The backsheet includes a film layer joined to a nonwoven layer. The absorbent article also comprises a wetness indicator disposed on the film layer. The wetness indicator includes a stabilizer, a colorant, and a matrix. The matrix includes a tackifier and at least one of a water-soluble polymer and a water-dispersible polymer. The wetness indicator exhibits no visible color change through the backsheet film layer after 10 days according to the CTH Stability Test.

DETAILED DESCRIPTION OF THE INVENTION

Figure 1:
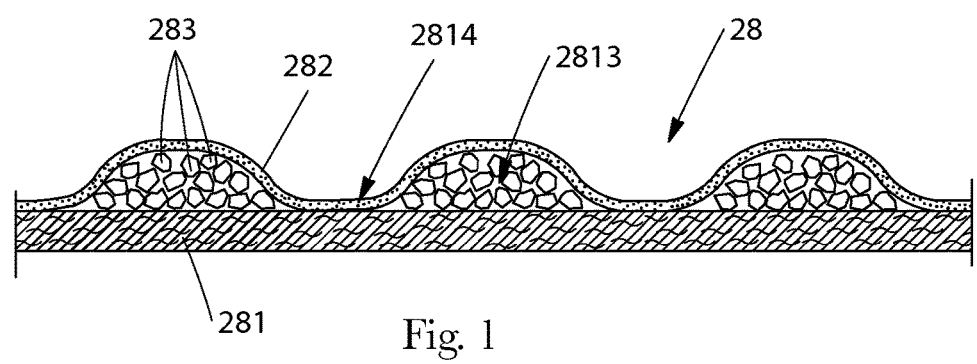
FIG. 1 is a schematic cross section view of an absorbent core.

It should be understood that every limit given throughout this specification will include every lower, or higher limit, as the case may be, as if such lower or higher limit was expressly written herein. Every range given throughout this specification will include every narrower range that falls within such broader range, as if such narrower ranges were all expressly written herein.

All percentages, ratios and proportions are by weight, and all temperatures are in degrees Celsius (° C.), unless otherwise specified. All measurements are in SI units unless otherwise specified.

"Absorbent article" refers to devices that absorb and contain body exudates, and, more specifically, refers to devices that are placed against or in proximity to the body of the wearer to absorb and contain the various exudates discharged from the body. Absorbent articles may include diapers, training pants (sometimes referred to as "closed diapers," "prefastened diapers," "pull-on diapers," "pants," and "diaper-pants, for example, see U.S. Pat. No. 5,246,433 to Hasse, et al.; U.S. Pat. No. 5,569,234 to Buell; or U.S. Pat. No. 6,120,487 to Ashton), adult incontinence undergarments, feminine hygiene products, breast pads, care mats, bibs, wound dressing products, and the like. As used herein, the term "body fluids" or "body exudates" includes, but is not limited to, urine, blood, vaginal discharges, breast milk, sweat and fecal matter.

"Absorbent core" means a structure typically disposed between a topsheet and backsheet of an absorbent article for absorbing and containing liquid received by the absorbent article and may comprise one or more substrates, absorbent polymer material disposed on the one or more substrates, and a thermoplastic composition on the absorbent particulate polymer material and at least a portion of the one or more substrates for immobilizing the absorbent particulate polymer material on the one or more substrates. In a multilayer absorbent core, the absorbent core may also include a cover layer. The one or more substrates and the cover layer may comprise a nonwoven. Further, the absorbent core is substantially cellulose free. The absorbent core does not include an acquisition system, a topsheet, or a backsheet of the absorbent article. Exemplary absorbent cores suitable for use herein may be found in US Pub. Nos. 2004/0162536 to Becker filed on Feb. 11, 2004; 2007/0167928 to Becker filed on Mar. 13, 2007; 2007/0179464 to Becker filed on Mar. 13, 2007; 2007/0156108 to Becker filed on Mar. 13, 2007; and 2004/0167486 to Busam filed on Feb. 11, 2004; U.S. Ser. Nos. 60/936,102 to Hundorf filed on Jun. 18, 2007; 60/936,109 to Hundorf filed on Jun. 18, 2007; 60/936,149 to Hundorf filed on Jun. 18, 2007; 60/936,085 to Ashton filed on Jun. 18, 2007; 60/936,084 to Ashton filed on Jun. 18, 2007; 60/936,150 to Ashton filed on Jun. 18, 2007; 60/936,146 to Asthon filed on Jun. 18, 2007; 60/936,037 to Ashton filed on Jun. 18, 2007; and 61/091,799 to Hundorf filed on Aug. 26, 2008.

"Absorbent polymer material," "absorbent gelling material," "AGM," "superabsorbent," and "superabsorbent material" are used herein interchangeably and refer to cross linked polymeric materials that can absorb at least 5 times their weight of an aqueous 0.9% saline solution as measured using the Centrifuge Retention Capacity test (EDANA 441.2-01).

"Airfelt" is used herein to refer to comminuted wood pulp, which is a form of cellulosic fiber.

"Comprise," "comprising," and "comprises" are open ended terms, each specifies the presence of what follows, e.g., a component, but does not preclude the presence of other features, e.g., elements, steps, components known in the art, or disclosed herein.

"Nonwoven" means a porous, fibrous material made from continuous (long) filaments (fibers) and/or discontinuous (short) filaments (fibers) by processes such as, for example, spunbonding, meltblowing, carding, and the like. Nonwovens do not have a woven or knitted filament pattern. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter ("gsm").

"Substantially cellulose free" is used herein to describe an article component, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core. Substantially cellulose free absorbent cores 10 may comprise absorbent polymer material 16 adhered to the dusting layer (e.g., 12) via thermoplastic adhesive material 18 forming a "complex" 14. The complex 14 may be in rows 20 (see FIG. 1).

"Substantially surfactant free" is used herein to describe an article component, such as a dusting layer, that contains less than 10% by weight of a surfactant or mixture thereof, less than 5% by weight of surfactant, less than 1% by weight of surfactant, no surfactant, or no more than an immaterial amount of surfactant where the surfactant may be anionic, cationic, nonionic, amphoteric or may include mixtures thereof and function to increase the wettability of the article component by reducing the contact angle of synthetic urine (as disclosed in U.S. Pat. No. 6,772,708 to Klofta) in contact with the surface of the article component (e.g., fibers of a nonwoven material or the surface of a film).

"Thermoplastic adhesive material" as used herein is understood to comprise a polymer composition from which fibers are formed and applied to the superabsorbent material with the intent to immobilize the superabsorbent material in both the dry and/or wet state. The thermoplastic adhesive material of the present invention forms a fibrous network over the superabsorbent material. Thermoplastic adhesive material may comprise one or a mixture of adhesives, including, but not limited to polymers such as polybutylene, copolymers such as styrenic block copolymers, tackifying resins, synthetic rubbers like those of the styrene butadiene and carboxylated styrene butadiene types, natural rubbers, waxes such as paraffin and microcrystalline waxes, oils such as mineral oil, opacifiers, anti-oxidants, and the like as is known in the art.

Wetness Indicator Composition

The wetness indicators described herein may be provided in the form of a composition that includes a colorant, a matrix, a stabilizer and optional additional ingredients. The wetness indicator compositions of the present invention may be applied to a structural component of an absorbent article. Substrates, disposable absorbent articles and structural components thereof are illustrated in more detail herein. It is believed, without being limited by theory, that the disclosed wetness indicators are especially suitable for use with absorbent articles such as diapers and pants that have a substantially cellulose free absorbent core (e.g., an absorbent core that utilizes superabsorbent polymer for substantially all of its absorbency).

The wetness indicator may be applied to a substrate or article component as a solid or a liquid composition. In certain embodiments, the wetness indicator may be applied as a hot-melt composition. That is, the wetness indicator may be heated to a particular temperature (i.e., melt temperature) and applied as a liquid. The melt temperature may vary as desired, as long as the wetness indicator exhibits desirable rheological properties (e.g., viscosity, melt flow rate, open time). The hot-melt wetness indicator may be applied by any suitable hot-melt applicator known in the art. For example, an applicator sold by the Nordson Corporation, Westlake, Ohio, as Part No. 7132378; SCSE-01 DL50 AB4 T.15, (a) Colorant In certain embodiments, the wetness indicator composition includes a colorant. The colorant may have a first color state, which is associated with a first wetness indicator state (e.g., dry). Examples of this first color state include, but are not limited to, colors visible to the human eye, such as red, blue, green, indigo, violet, yellow, orange, purple, and the like; electromagnetic radiation that is not typically visible to the unaided human eye, such as ultraviolet ("UV") or infrared ("IR") radiation, and the like. The first color state may be invisible, white, black, translucent or opaque. The colorant(s) also has a second color state, which is associated with a second wetness indicator state (e.g., wet). Examples of this second color state include, but are not limited to, colors visible to the human eye, such as, red, blue, green, indigo, violet, yellow, orange, purple, and the like; electromagnetic radiation that is not typically visible to the unaided human eye, such as UV or IR radiation and the like. The second color state may be invisible, white, black, translucent, opaque, or have a change in intensity or visual distinctiveness, and the like, when compared to the first color state. The first color state of the colorant is different, in some form, from the second color state. For example, the first color state may be a first color such as yellow, while the second color state may be a different color such as blue; or the first color state may be a first color such as blue, while the second color state may be transparent and/or a wavelength of electromagnetic radiation not typically visible to the unaided human eye.

In certain embodiments, the first color state is associated with a first wetness indicator state. This first wetness indicator state may include, but is not limited to: a specific pH or pH range; absence or presence of a specific compound or compounds such as water, urea, dissolved oxygen, ions such as, but not limited to, iron, calcium, magnesium, zinc, sodium, chloride, protons, hydroxide and combinations thereof, sugars such as glucose, enzymes, biological materials in the urine and/or feces; and combinations thereof; microbiological flora and fauna such as bacteria and the like; some threshold level of a compound or composition, such as, water, urine, etc.; and combinations thereof.

In certain embodiments, the second color state is associated with a second wetness indicator state. The second wetness indicator state may include, but is not limited to: a specific pH or pH range; absence or presence of a specific compound or compounds such as water, urea, dissolved oxygen, ions such as, but not limited to, iron, calcium, magnesium, zinc, sodium, chloride, protons, hydroxide and combinations thereof, sugars such as glucose, enzymes, biological materials in the urine and/or feces; and combinations thereof; microbiological flora and fauna such as bacteria and the like; some threshold level of a compound or composition such as water, urine, menses, blood and the like; and combinations thereof.

In certain embodiments, the first wetness indicator state is a specific pH or pH range and the second wetness indicator state is a specific pH or pH range different from the specific pH or pH range of the first wetness indicator state. For example, the second wetness indicator state may be the pH or pH range of urine (e.g., human urine), as measured as a neat solution at human body temperature (typically 37.6° C.). The pH range of human urine is typically between 5.5 and 8.0. In this example, the first wetness indicator state may be a specific pH or pH range which is more acidic or more basic than the second wetness indicator state, that is, a pH of less than 5.5 or greater than 8.0. In this example, the colorant may be a pH indicator selected to signal a change from the first wetness indicator state to the second wetness indicator state (e.g., initiated by a urination event). Non-limiting examples of suitable pH indicators include those disclosed in U.S. Pat. No. 6,904,865 to Klofta.

Nonlimiting examples of colorants include sulfonephthalein pH indicators such as, but not limited to, bromocresol green, bromocresol purple, m-cresol purple, cresol red, chlorophenol red, bromothymol blue, bromopyrogallol red, bromoxylenol blue, bromophenol blue, and combinations thereof. In an acidic state, the sulfonephthalein class of indicators are most commonly yellow in color. Upon contact with liquid such as urine, which has a sufficiently high pH, the color of the colorant will change. For example, the sulfonephthalein class of pH indicators typically change to a green, blue, or purple color.

In certain embodiments, the wetness indicator composition may include two or more colorants, each colorant having different first and/or second colorant states or being associated with a different wetness indicator state (e.g., different $pK_a$ values, a pH and an enzyme trigger, a pH trigger, colors, solubilities, or other properties). The varying first and second colorant and/or wetness indicator states may facilitate interactive scenes, sequences, or displays providing information regarding relative fullness/wetness of the article or merely provide entertainment and/or aesthetic value. For example, the wetness indicator may include one colorant that turns blue and another that turns red upon contact with urine. Alternatively or additionally, one portion of a graphic in the wetness indicator may appear and another portion may disappear upon contact with the activating liquid. In certain embodiments, a small quantity of an oil soluble dye such as D&C red or D&C yellow may be included to change the first and/or second states of a colorant. This may provide color changing combinations that are more aesthetically pleasing. It is to be appreciated that embodiments including two or more colorants having the same first and second colorant states and/or associated with the same wetness indicator state are also contemplated herein.

The colorant may be employed in wetness indicator compositions at levels which are effective at indicating the presence of a liquid, and include from 0.1% to 5%, from 0.5% to 2%, from 1% to about 1.5%, and any value in these ranges, by weight of the wetness indicator composition.

(b) Matrix

In certain embodiments, the wetness indicator composition may include a matrix. The matrix generally acts to hold the colorant in place before, during, and/or after contact with liquid. The matrix desirably provides the colorant with resistance to leaching and premature activation, especially in high humidity environments. Upon contact with a particular composition (e.g., urine, fecal material, menses, or blood), the matrix desirably allows sufficient liquid to contact the colorant to effect a change in appearance, but inhibits the colorant, in either its first color state or second color state, from leaching out of the wetness indicator and into the surrounding environment (e.g., into the absorbent core of a disposable absorbent article).

When the wetness indicator is applied to a substrate, the matrix and consequently the wetness indicator composition, should have sufficient wet and dry cohesion, adhesion, and/or flexibility to remain fully retained on the substrate. In other words, the wetness indicator should retain sufficient flexibility, cohesion, and/or adhesion to minimize and, ideally, prevent portions of the wetness indicator from separating from itself and/or the substrate (e.g., prevent chipping, flaking, or cracking). Thus, the matrix may aid not only in preserving and inhibiting the leaching of the colorant, but also in maintaining the structural integrity of the wetness indicator composition in the dry and/or wet states.

(i) Tackifier

The matrix may include one or more so-called tackifiers. Tackifiers are known in the adhesive art as compositions that increase the tackiness of an adhesive (i.e., facilitate the ability of the adhesive to form a bond with a surface or composition upon contact). Nonlimiting examples of tackifiers include rosins, rosin esters, polymerized rosins, pentaerythritol rosin esters, styrenated terpenes, polyterpene resins, terpene phenolics, and combinations thereof. Particularly suitable examples of rosins includes Arizona Chemical's SYLVATAC RE98 brand rosin ester, which is a pentaerythritol rosin ester or a hydrogenated rosin sold under product code Foral AX-E by Eastman Chemical Company, Kingsport, Tenn.

In addition to being tackifiers, rosin esters, polymerized rosins, and pentaerythritol rosin esters may also be effective solubilizers for some of the other ingredients in a wetness indicator composition. While not wishing to be limited by theory, it is believed that the acidity of some rosin esters, polymerized rosins and pentaerythritol rosin esters contribute to the stabilization of particular colorants such as the pH indicators described above (i.e., inhibit or prevent premature color change/activation). For example, some rosins contain acidic carboxylate groups that may aid in keeping a colorant like bromocresol green in its acidic yellow state. Examples of acidic rosins include Eastman's Foral AX-E, and Resin P, available from Resinas Sintéticas, Inc., Mexico. In certain embodiments, the acidic yellow state is the preferred first color state associated with the first wetness indicator state (e.g., dry state) when a pH indicator such as bromocresol green is used as a colorant.

The tackifier may be selected to immobilize the colorant in its first color state. How the tackifier immobilizes the colorant typically depends on what the tackifier and colorant are. For example, the tackifier may immobilize the colorant when the colorant is in its first color state by one or more forces selected from the group consisting of adhesion, hydrogen bonding, ionic, polar covalent bonding, Van der Waals forces, dipole-dipole forces, London dispersion forces and combinations thereof.

The tackifier may be employed in compositions at levels which are effective at immobilizing and stabilizing the colorant in its first state, including from 20% to 50%, from 25% to 45%, and from 30% to 40%, by weight of the wetness indicator composition.

(ii) Water-Soluble or Water-Dispersible Polymer

The matrix may include one or more water-soluble or water-dispersible polymers or chemicals. The wastersoluble or water-dispersible polymers or chemicals may be selected to aid in immobilizing a colorant when the colorant is in its second color state. Nonlimiting examples of water-soluble or water-dispersible polymers or chemicals for use in wetness indicator compositions may be found in U.S. Pat. No. 6,904,865 to Klofta. Other nonlimiting examples of water-soluble or water-dispersible polymers or chemicals include quaternary ammonium salt compounds, cationic clay, polyacrylic acid polymers, organic acids, and combinations thereof. Examples of suitable quaternary ammonium compounds include, but are not limited to, dimethyl(2-ethylhexylhydrogenatedtallowalkyl)ammonium methyl sulfate, cocoalkylmethyl[ethoxylated(15)] ammonium chloride, dodecyltrimethyl ammonium chloride, hexadecyltrimethyl ammonium methyl sulfate, octadecyltrimethyl ammonium chloride, dicocoalkyldimethly ammonium chloride, di(hydrogenated tallowalkyl)dimethyl ammonium chloride, and distearyldimethyl ammonium chloride. It should be noted that the counter anion associated with a quaternary ammonium compound, or other water-dispersible polymer or chemical having one or more cationic groups, is not specifically limited to chloride. Other anions can also be employed and non-limiting examples include methyl sulfate and nitrite. Similarly, any suitable counter cation, such as, but not limited to, sodium, potassium, calcium, magnesium, zinc, protons, ammonium, substituted ammonium and the like, may be associated with a water-dispersible polymer or chemical having one or more anionic groups.

A particularly suitable water-soluble polymer is polyethylene glycol ("PEG"). In certain embodiments, it may be desirable to include two or more different molecular weight PEGs, where at least one of which is a lower molecular weight PEG to provide desirable kinetics since it is hydrophilic, and at least one of which is a higher molecular weight PEG to provide a desirable melting temperature and/or open time for the wetness indicator.

How the water-soluble or water-dispersible chemical or polymer immobilizes the colorant when in its second color state typically depends on the chemical composition of the water-soluble or water-dispersible chemical or polymer and the colorant. For example, if the colorant takes the form of an anionic long chain molecule and the water-soluble or water-dispersible chemical or polymer is a cationic molecule, then the bond formed may be, for example, an ionic bond, a covalent bond, or the like. In another example, if the colorant takes the form of a cationic molecule and the water-soluble or water-dispersible chemical or polymer is an anionic long chain molecule, then the bond formed may be, for example, an ionic bond, covalent bond, or the like. The water-soluble or water-dispersible chemical or polymer may immobilize the colorant when the colorant is in its second color state with covalent bonds, ionic bonds, hydrogen bonds, Van der Waals force, and combinations thereof.

Without wishing to be bound by theory, it is believed that when the colorant is an anion in its second color state and the water-soluble or water-dispersible chemical or polymer is a cation, or the colorant is a cation in its second color state and the water-soluble or water-dispersible chemical or polymer is an anion, the water-soluble or water-dispersible chemical or polymer forms an ionically bonded coacervate with the colorant. For example, when the second wetness indicator state associated with a colorant's second color state is the pH of urine, contacting the wetness indicator with urine will change the colorant to its second color state, i.e., an anion. The anionic colorant forms an ionic bond with the cationic water-soluble or water-dispersible chemical or polymer. It is believed, without being limited by theory, that the resulting coacervate forms due to the strong coulombic interaction between the opposite charges of the colorant and the water-soluble or water-dispersible chemical or polymer. The coacervate formed between the colorant and the water-soluble or water-dispersible chemical or polymer neutralizes the charge in both species, dramatically reducing the solubility of the coacervate in polar solvents such as water or urine. Due to the lipophilic natures of the matrix, however, the solubility of the coacervate in the matrix remains relatively high due to the charge neutralization. The combination of decreased solubility in polar solutions and increased solubility in nonpolar solutions decreases the tendency of the colorant to leach out of the matrix. Further, the increased lipophilicity of the coacervate leads to increased intermolecular bonding forces between the coacervate and other components of the matrix. These intermolecular forces may further limit the diffusion and mobility of the colorant in an aqueous environment such as urine.

In certain optional embodiments, use of cationic quaternary ammonium compounds may also function to darken or intensify the color change of certain colorants, especially those belonging to the sulfonephthalein class of pH indicators. Without wishing to be bound by theory, it is believed this darkening is due to several possible factors: 1) alkaline impurities within the quaternary ammonium raw material, 2) absorption shifting and absorptivity coefficient increases due to coacervate formation and/or 3) increased formation of the colorant in its second color state.

The water-soluble or water-dispersible chemical or polymer may be employed in wetness indicator compositions at levels which are effective at immobilizing the colorant in its second state, including from 20% to 50%, from 25% to 45%, and from 30% to 40%, by weight of the wetness indicator composition.

Stabilizer Ingredient

Suitable wetness indicators for use herein should not activate prematurely (i.e., indicate a change from the first wetness indicator state to the second wetness indicator state). Thus, it may be desirable to include a stabilizer when the colorant is a pH indicator and when the absorbent article could be stored under conditions of high humidities and temperatures and/or in close proximity to a pH altering composition (e.g., superabsorbent polymers). The inclusion of a stabilizer within the wetness indicator composition may be especially important for new diaper designs where materials and/or chemicals are present that could potentially prematurely activate the color change of the colorant within the wetness indicator composition (e.g., diapers that have an absorbent core made almost entirely of superabsorbent polymer).

In certain embodiments, the stabilizer may be an acidic stabilizer. The inclusion of a stabilizer, while not wishing to be limited by theory, is believed to play a role in stabilizing the colorant against premature changes caused by exposure to humid environments and/or certain components of the diaper, by maintaining a stable pH, such as a low pH environment with an acidic stabilizer, around the colorant even when the wetness indicator is exposed to high humidities and/or certain components of the diaper. This maintenance of a stable pH environment keeps the colorant, especially when the colorant is a pH indicator, in its first color state.

It may be desirable for the colorant of a wetness indicator to maintain its first color state during a variety of storage and packaging conditions while still undergoing a noticeable color change in a reasonable amount of time after being contacted by urine. The colorant should also remain stable in the presence of various chemicals and materials that might be present in a disposable diaper (e.g., surfactants and superabsorbent polymers). Although acidic moieties present in the rosins as part of the matrix may aid in preserving the first color state, additional stabilizer ingredients may be desirable in some new diaper designs (e.g., where high pH components within the diaper can cause the undesirable and premature color change activation of the colorant). For example, a colorant that has a first color state associated with a dry, relatively low pH wetness indicator state, may require the addition of acids of suitable strength and/or concentration to maintain the colorant in its first color state when positioned proximate to high pH components and/or in a high humidity environment.

For a pH indicator colorant such as bromocresol green, which changes color between a pH of 3.8 and 5.4 (see "The Sigma-Aldrich Handbook of Stains, Dyes and Indicators," by Floyd J. Green, Aldrich Chemical Co., Milwaukee, Wis.), the stabilizer should contribute suitably strong acidic moieties at a desired concentration to keep the bromocresol green in its yellow state within the matrix prior to a desired activation event (e.g., urination). Although many strong acids like sulfuric acid and hydrochloric acid have suitably low pH's to accomplish this, their solubilities are low in an anhydrous matrices such as those typically present in unused disposable absorbent articles. In addition, the high acidity typically associated with such acids may chemically decompose one or more components present in the wetness indicator and/or diaper. As noted previously, carboxylic acid moieties present in the matrix ingredients (e.g., rosins) may aid in maintaining the colorant in its acidic color state, but are typically too weak to maintain the dry, yellow-color state of bromocresol green if it is exposed to high humidities and/or high pH components of a diaper. To increase the stability of the carboxylic acid moiety, it may be desirable to add electron withdrawing groups between the carboxylic acid moiety and another portion of the molecule. For example, a fatty acid like stearic acid can be made more acidic (i.e., made a stronger acid) by inserting polyoxyethylene groups between the carboxylic acid group and the alkyl chain. These types of molecules are sometimes referred to as ether carboxylates and, due to their acidity, can be effective in maintaining the dry state acid form of a pH indicator colorant like bromocresol green. In addition, the hydrophobic alkyl group present in ether carboxylates may act to increase the solubility within the wetness indicator matrix. After being contacted with urine, the ether carboxylate may become anionic and form a coacervate complex with a cationic colorant. Due to charge neutralization of this coacervate complex and the presence of hydrophobic alkyl groups, the coacervate complex would have a lower solubility in the hydrophilic urine so leaching would be inhibited. Finally, the ether carboxylate's surfactancy may aid in increasing the kinetics for activating the color change of the wetness indicator composition after it is contacted by urine.

Other examples of stabilizers include, without limitation, monoalkyl phosphate free acids and dialkyl phosphate free acids. The phosphate acid moiety is a stronger acid than the carboxylic acid group and thus can be more effective in maintaining the low pH environment required to keep the pH indicator colorant in its dry acidic state. These alkyl phosphate free acids have been found to be particularly effective in preserving the first, unactivated color state (i.e., yellow) of the bromocresol green colorant from premature activation due to, for example, high humidities or destabilizing materials and/or chemicals present in certain diaper designs. Particularly effective alkyl phosphate free acids are monostearyl phosphate acid, monocetyl phosphate acid, monocetearyl phosphate acid, distearyl phosphate acid, dicetyl phosphate acid, and dicetearyl phosphate and other monoalkyl and dialkyl types of phosphate acids. Thus, these phosphate acids are suitably strong acids to maintain the pH indicator colorant in its first, unactivated color state, and the lipophilic alkyl moiety aids in increasing its solubility within the wetness indicator composition. In addition, the surfactant nature of the alkyl phosphate free acids can aid in speeding up the kinetics of the color change after the wetness indicator composition is contacted by urine. Finally, after deprotonation and becoming anionic due to contact by urine, the negatively charged phosphate group can form a coacervate complex with a cationic colorant.

Other acidic stabilizers which are particularly effective in stabilizing the wetness indicator formula to relatively high humidity and/or destabilizing components within the diaper include, but are not limited to: organic acids, such as, but not limited to, fatty acids such as stearic acid, palmitic acid, lower molecular weight acids such as citric acid, malic acid, maleic acid, lactic acid, glycolic acid, gluconic acid, fumaric acid, adipic acid, ascorbic acid, and salicylic acid; acid esters, such as, citrate esters, e.g., monostearyl citrate and monocetyl citrate, glycolate esters, lactate esters; phosphorus containing organic acids, such as, monostearyl phosphate and monocetyl phosphates; ether carboxylic acids; N-acyl sarcosinic acids; N-acyl glutamic acids; N-acyl ethylenediaminetriacetic acid; alkane sulfonic acids; alpha-olefin sulfonic acids; alpha-sulfonic acid fatty acid methyl esters; sulfate esters; inorganic acids, such as, phosphoric acid; and combinations thereof. Examples of suitable basic stabilizers include, but are not limited to: monoethanolamine; diethanolamine; triethanolamine; dipropylenetriamine; diiosopropyl amine; organic diamines, such as, but not limited to, 1,3-bis(methylamine)-cyclohexane, 1,3-pentanediamine; inorganic bases, such as, but not limited to, sodium hydroxide, magnesium hydroxide, and combinations thereof.

The stabilizer, when present as a fatty acid is typically employed in compositions at levels which are effective at stabilizing the colorant, for example, from 20% to 40% or from 25% to 35%, by weight of the wetness indicator composition. When the stabilizer is present as a phosphate or sulfate free acid, the amount of stabilizer required to provide suitable stabilization of the colorant may decrease, since these are typically stronger acids than those of the fatty acid type (i.e., carboxylate). For example, a level of 1 to 5% by weight of a monoalkyl phosphate acid may be suitable to stabilize the wetness indicator composition in its dry state.

Optional Additional Ingredients

In one optional embodiment of the present invention, the wetness indicator composition may include optional ingredients, including, but not limited to, surfactants, structural adjuncts, rheology modifiers (e.g., viscosity modifiers) and combinations thereof. The optional additional ingredients, when present, are typically employed in compositions at levels which are effective at providing the benefits of the optional additional ingredient or ingredients, including from about 0.001% to about 50%, from about 0.1% to about 40%, and from about 1% to about 35%, by weight of the composition. The optional ingredients and amounts disclosed in U.S. Pat. No. 6,904,865, issued Jun. 14, 2005 to Klofta, et al. may be used in the wetness indicator compositions of the present inventions.

Substrate

The wetness indicator composition may be disposed on and/or in a substrate. When present on a substrate, it may be desirable to position the wetness indicator composition on and/or in a portion of substrate that is likely to be contacted by a liquid such as water, urine, menses, blood and the like. The substrate may include, but is not limited to, woven fabrics, nonwoven fabrics, films, sponges, and combinations thereof. The substrate may comprise synthetic and/or natural materials. In certain embodiments, the substrate may be an article in its own right, such as, a continuous nonwoven fabric. In certain embodiments, the substrate may be configured, individually or in combination with other elements, as one or more structural components of an absorbent article, including, but not limited to, the outer cover, the backsheet, the topsheet, fasteners, absorbent material, etc. In one optional embodiment, the wetness indicator composition may be applied to the absorbent article as a whole.

The wetness indicator may be applied to a substrate via any means of liquid or semi-liquid application as known in the art, including, but not limited to, slot coating, spraying, gravure printing, ink jet printing, and digital printing. Alternatively, the wetness indicator may be a solid or semi-solid material affixed to a substrate via adhesive bonding, chemical bonding or intermolecular force bonding. Multiple indicators may be applied to the same substrate in overlapping or non-overlapping geometries. The solidification process may be accelerated via the use of convective mass transport, if evaporation of a solvent is required, or convective or conductive heat transfer, e.g., cooling via air or chilled rolls, etc.

It may be desirable that the wetness indicator contact, adhere to, or be in liquid communication with one or more adjacent substrates (e.g., the dusting layer) in addition to the substrate to which it has been applied (e.g., backsheet or outer cover) to ensure desirable wicking of fluid (e.g., urine) to the wetness indicator composition after the occurrence of a wetness event. That is, when a gap exists between the wetness indicator composition and an adjacent substrate (e.g., the dusting layer), fluid may not travel from the absorbent core to the wetness indicator within the desired time to signal the occurrence of a wetness event. Thus, it may be desirable to apply the wetness indicator composition at a suitable predetermined temperature such that effective coating of both the backsheet and the dusting layer occurs without bleeding of the composition to regions within the diaper, which may undesirably impact the colorant's stability.

It may additionally be desired that there is substantial contact/adherence/liquid communication to the adjacent substrate to ensure that the wetness indicator composition is evenly (top to bottom and side to side) wetted and thus provides the full signal intended. This can be accomplished by providing a wetness indicator composition that has a sufficient open time (i.e., the wetness indicator is tacky enough for a long enough time to adhere to the substrate, but not so long that it bleeds through the substrate).

Bleeding through becomes a larger issue when the substrate is a lower basis weight and/or breathable film or nonwoven. Modern absorbent articles may use backsheets having a basis weight less than 60 gsm, less than 40 gsm, or less than 20 gsm. The backsheets may be breathable, having water vapor transmission rates (according to ASTM E-96/E-96M-05) of greater than 100 $g/m^2/24$ hr (grams of water vapor per square meter per 24 hour period), greater than 1000 $g/m^2/24$ hr, or even greater than 5000 $g/m^2/24$ hr, but typically less than 23,000 $g/m^2/24$ hr. The backsheets disclosed herein may be configured as a single layer of material or as a laminate material. For example, the backsheet may be a laminate material formed by joining an elastomeric film layer to an extensible nonwoven layer. In this example, the elastomeric film layer may be formed from a styrenic block copolymer or an elastomeric polyolefin (e.g., VISTAMAXX brand elastomeric polypropylene resin available from Exxon Chemical Company), and the nonwoven layer may include mono-component and/or multi-component fibers. If multi-component fibers are selected, they may be core/sheath-type bicomponent fibers, which are configured such that the core includes polypropylene and the sheath includes polyethylene or vice versa). Alternatively or additionally, the fibers of the nonwoven layer may be elastomeric and include an elastomeric polyolefin. In certain embodiments, the backsheet may be a laminate material formed by sandwiching an elastomeric film layer between two nonwoven layers. It is to be appreciated that a single nonwoven layer may be formed from one or more layers of the same or different fibers (e.g., a nonwoven layer formed as three layers of fibers in a spunbond-meltblown-spunbond configuration).

Further, nonwoven dusting layers (as well as, intermediary layers between the wetness indicator composition and the dusting layer) may have a mean flow pore (according to ASTM F316-86) size of greater than 1 micron or greater than 10 microns, but typically less than 100 microns. Suitable substrates (e.g., dusting layer or intermediate layers) may have a hydrohead value of greater than 1 mm of water, greater than 10 mm of water, or greater than 100 mm of water, but typically less than 150 mm water as measured by AATCC 127-1985 titled "Rising Column Strike Through." And, nonwovens and intermediary layers may have a basis weight of less than 50 $g/m^2$, less than 30 $g/m^2$, or less than 15 $g/m^2$. Nonwovens and intermediary layers of the present invention may comprise fibers having a diameter of less than 200 microns, less than 20 microns, or less than 2 microns. And, the fibers may be shaped (i.e., having a non-round cross-section), including multilobal (e.g., bilobal, trilobal fibers, etc.).

In embodiments where the wetness indicator composition is in direct contact with the outer face (i.e., garment facing side) of the dusting layer, the dusting layer may have thermoplastic adhesive material and absorbent polymer material adhered to its inner face (i.e., wearer facing side). In such an embodiment, the area of the outer face of the dusting layer that is adhered/contacting the wetness indicator may be from about 0.01 $cm^2$ to about 200 $cm^2$, from about 1 $cm^2$ to about 50 cm2, or from about 3 $cm^2$ to about 20 $cm^2$. And the amount of thermoplastic adhesive material and absorbent polymer material adhered to inner face of the dusting layer that corresponds to the outer face contacting the wetness indicator may be from about 1 $g/m^2$ to about 300 $g/m^2$, from about 10 $g/m^2$ to about 200 $g/m^2$, or from about 25 $g/m^2$ to about 150 $g/m^2$. This is the complex of thermoplastic adhesive material and absorbent polymer material largely responsible for prematurely changing the color of the wetness indicator composition.

Wetness indicators suitable for use with the lower basis weight and/or breathable films and nonwovens described above include compositions of straight chain alkyl moieties (which are correlated with the open time of the wetness indicator) having a chain length from about C12 to about C300, from about C14 to about C100, or from about C16 to about C50. Further, the wetness indicators herein may be applied at a basis weight of greater than about 10 $g/m^2$, greater than about 20 $g/m^2$, or greater about 25 $g/m^2$, but typically less than 100 $g/m^2$. Further more, suitable wetness indicators that include a phosphate free acid may have a phosphorous content of 10.0% or less, of 1.0% or less, or of 0.1% or less.

In one exemplary embodiment, the wetness indicator may initially be applied as a molten composition to an inner face (i.e., the wearer facing side) of the backsheet of a diaper such that it adheres to the backsheet. Then, the outer face (i.e., the garment facing side) of the dusting layer of the diaper may be brought into contact with the wetness indicator such that the wetness indicator contacts/adheres to the dusting layer over the entire (or substantially entire) surface of the wetness indicator. In this example, the wetness indicator is in liquid communication with the absorbent core (i.e., the dusting layer is disposed between the backsheet and core), and therefore can provide a wetness event signal visible from outside the substrate when the product is being worn (i.e., visible to a wearer, a caregiver, parent and the like). In certain embodiments, the colorant visibly changes from its first color state to its second color state within a short time after the wetness indicator is contacted with a suitable liquid, for example, within 15 minutes, 10 minutes, 5 minutes, or 1 minute, but typically more than 30 seconds after the liquid contacts the wetness indicator.

In certain embodiments, the substrate or absorbent article comprising the substrate may be configured to allow suitable liquids to contact the wetness indicator in certain regions of the substrate or absorbent article at various loading levels. For example, a disposable diaper may be designed to allow urine to contact the wetness indicator located in the crotch region of the product on the first urination, but contact the wetness indicator disposed in other regions of the disposable diaper only after the amount of urine in the disposable diaper reaches a predetermined threshold value. For example, the absorbent core of the disposable diaper may have limited ability to distribute urine from a one portion of the absorbent core to another portion of the absorbent core (e.g., from the point of insult to a lateral portion spaced away from the insult) until a threshold amount of urine has been received by the core. When the amount of urine reaches the threshold amount, the urine may be distributed to other areas of the diaper, causing the colorant in these areas to change from a first color state to a second color state. As the total urine loading in the disposable diaper increases, more areas of the absorbent core will contain sufficient urine to change the colorant in a wetness indicator that may be located in those areas from a first color state to a second color state.

The wetness indicator compositions may be present on a substrate in any desired pattern or configuration, including, but not limited to, stripes, dots, regular shapes, irregular shapes, alphanumeric characters, pictorial representation of animals, pictorial representation of inanimate objects, cartoon characters, anthropomorphic images, logos, trademarks and any combination or arrangement thereof. The wetness indicating compositions may be applied in any pattern or in conjunction with permanent graphics, such as, permanent graphics on the outer surfaces of a disposable absorbent article or component thereof.

In certain embodiments, the wetness indicator, when present on a substrate, may be applied at levels that are effective at providing visible signals, including from 1 gsm to 100 gsm, from 5 gsm to 75 gsm, 10 gsm to 60 gsm, from 20 gsm to 50 gsm, or even from 30 gsm to 40 gsm. However, it is to be understood that the amount of wetness indicator present on a substrate will depend upon many factors such as, but not limited to, substrate type (e.g., thick, thin, opacity, bulky, dense, other physical properties), substrate material, intended use of the substrate (e.g., disposable diaper, panty liner, bandage), method used for applying the wetness indicator compositions, desired intensity of signal in either dry or after contacting liquid, desired kinetics for the color change, desired stability of the color within the wetness indicator composition, desired pattern or configuration of the wetness indicator composition on substrate, and combinations thereof.

One particularly suitable example of a wetness indicator is a hot-melt wetness indicator sold under the product code H9567 by the Bostik Corporation, Wauwatosa, Wis. The H9567 hot-melt wetness indicator may be desirably applied to the backsheet of a disposable diaper. The backsheet may be formed as a bilaminate material (e.g., a 25 micron breathable film joined to a 25 gsm nonwoven material), with the wetness indicator being applied to the inner face (i.e., wearer facing side) of the film layer of the backsheet. In this example, the H9567 wetness indicator exhibits no color change after more than 75 days when tested according to the CTH Stability Test method described hereinbelow. Further, the H9567 wetness indicator exhibits suitable colorant kinetics, according the Colorant Kinetics Test.

Additional information on incorporation of wetness indicating compositions in and/or on substrates and/or disposable absorbent articles can be found disclosed in U.S. Pat. No. 4,022,211 issued, on May 10, 1977, to Timmons; U.S. Pat. No. 6,297,42, issued on Oct. 2, 2001, to Olson; U.S. Pat. No. 6,307,119 issued on Oct. 23, 2001 to Cammarota; and U.S. Patent Applications Nos. 20020007162A1 entitled "Absorbent articles having wetness indicating graphics incorporating a training zone," filed on Aug. 13, 2001, published Jan. 17, 2002, in the name of Cammarota; and 20010053898A1 entitled "Absorbent articles having wetness indicating graphics providing an interactive training aid" filed on Jul. 24, 2001, published Dec. 20, 2001, in the name of Olson; and WO 00/76438 published on Dec. 21, 2000, and assigned to Kimberly-Clark Worldwide Inc., and WO 00/76443 published on Dec. 21, 2000, and assigned to Kimberly-Clark Worldwide Inc.

The absorbent core of a modern disposable absorbent article may include little or none of the cellulosic material typically included in the absorbent core of a traditional diaper or pant. As discussed previously, these so-called "air-felt free" cores may pose additional problems when used with traditional wetness indicators (e.g., premature triggering due to a chemical reaction between the absorbent material and the wetness indicator). An example of an air-felt free core is shown in FIGS. 1-3, as described below.

FIG. 1 shows a schematic cross-section view of an example of a suitable absorbent core absorbent core 28 that is substantially cellulose free. The absorbent core 28 shown in FIG. 1 includes first and second webs of material 281, 282 and an absorbent material 283 disposed between the first and second webs 281, 282. The first and/or second web 281, 282 may be a fibrous material chosen from at least one of a nonwoven web, a woven web and a layer of thermoplastic adhesive material. The first and second webs 281, 282 may be made of the same or different materials. For example, the first web 281 may be a nonwoven web and the second web 282 may be a layer of thermoplastic adhesive material. The absorbent core 28 may include absorbent material 283 disposed between the first and second webs 281 and 282. For example, the absorbent material 283 may be deposited on the first surface 2811 of the first nonwoven 281 in a substantially discontinuous pattern to form absorbent material containing regions 2813 and non-absorbent material containing region 2814 on the first web 281. The absorbent material containing regions 2813 include most or even all of the absorbent material 283 in the absorbent core 28, while the non-absorbent material containing regions 2814 include little or even none of the absorbent material 283. The discontinuous deposition of absorbent material 283 on the first layer 281 may impart an essentially three-dimensional structure to the second web 282. In other words, the second web 282, when applied as a layer of thermoplastic adhesive material, follows the topography of the discontinuously deposited absorbent material 283 on the first nonwoven web 281.

Figure 2:
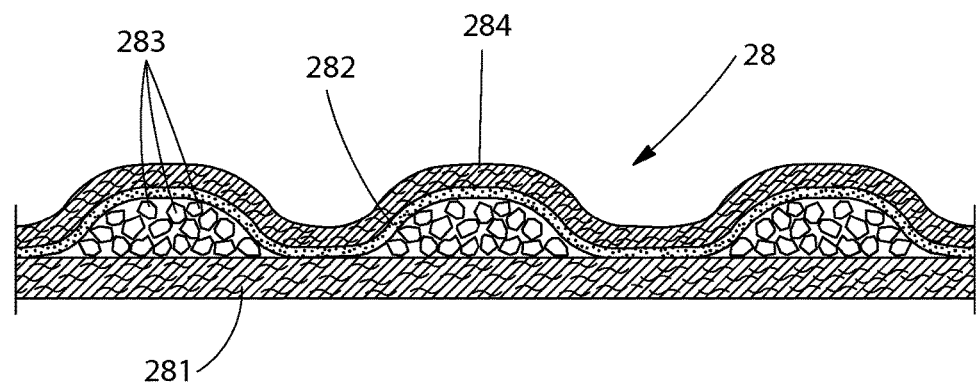
FIG. 2 is a schematic cross section view of an absorbent core.

FIG. 2 shows an exemplary embodiment of an absorbent core 28 that includes a third web of material 284. This third web 284 may be a nonwoven material and may function as a so-called "core cover." In certain embodiments, the surface energy of the first web 281 may be different from the surface energy of the third web 284. For example, the surface energy of the third web 284 may be greater than the surface energy of the first web 281 such that certain liquids (e.g., water and urine) penetrate the third web 284 to reach the absorbent material 283, but are prevented or at least inhibited from undesirably penetrating the first web 281. This may be particularly advantageous when the first web 281 is positioned against the backsheet of an absorbent article, for example, as a dusting layer. The different surface energies of each web 281, 284 may be obtained, for example, by applying different amounts of surfactant to the first and third webs 281, 284 or applying no surfactant to one of the webs 281 and some surfactant to the other web 284. In another example, different surface energies may be obtained by applying a different type of surfactant to the first web 281, relative to the third web 284. In certain embodiments, the first and third webs 281, 284 may also be different structurally. For example, the third web 284 may be formed from one or more layers of spunbond fibers whereas the first web 281 includes one or more layers of spundbond fibers and one or more layers of meltblown fibers. The third web 284 may applied directly on top of the first web 281, the absorbent material 283 and/or the second web 282. As a result, the first and third webs 281 and 284 may function to further encapsulate and immobilize the absorbent material 283.

Figure 3:
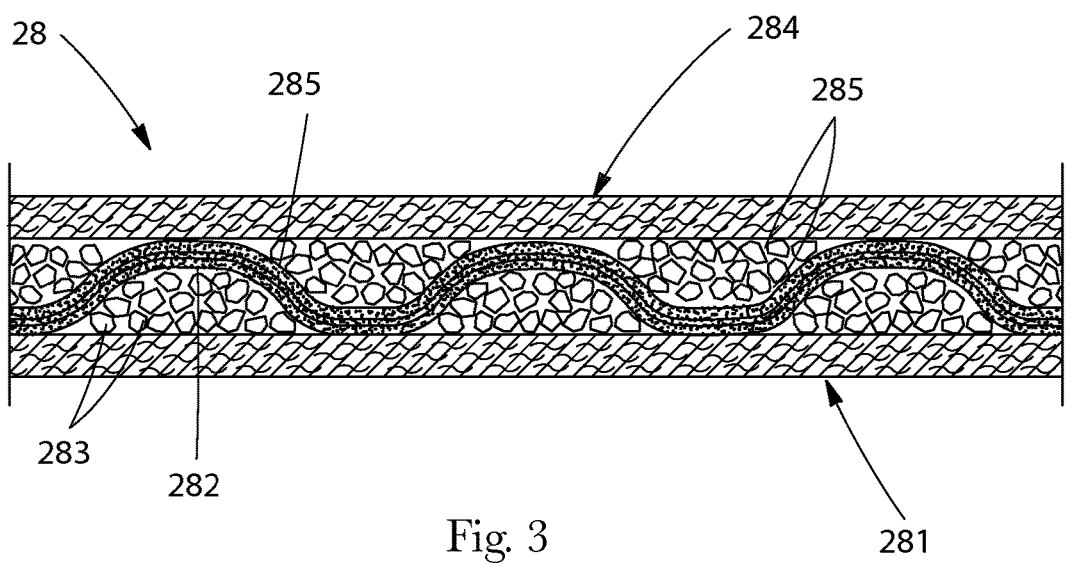
FIG. 3 is a schematic cross section view of an absorbent core.

FIG. 3 shows an exemplary embodiment of an absorbent core 28 wherein a thermoplastic adhesive material 285 is applied on top of the third web 284 as previously described in the context of the first web/absorbent material/second web 281/283/282 composite (i.e., a second composite is formed from the third web/absorbent material/fourth web 284/283/285). The pattern of absorbent material 283 present on the third web 284 may be the same as or different from the pattern of absorbent material 283 present on the first web 281. It is believed that when the patterns of absorbent material that are present on the first and second webs are different, each web/absorbent composite may have different functionalities such as for example, different absorbent capacities and/or different acquisition rates of liquids.

TEST METHODS

A. Controlled Temperature and Humidity (CTH) Stability Test Method:

For premade products (e.g., diapers purchased from a retail store), place 10 products to be tested in controlled temperature and humidity (CTH) room, as described hereinbelow. For handmade samples, follow the entire procedure outlined below.

Heat the wetness indicator to a temperature that is approximately 10° C. above its melting point. For the Samples shown in Tables 1 and 2 below, this temperature is typically in the range of 90° C. to 110° C. At this same temperature, a stainless steel bird applicator (Gardco Model Number AP-6X002ts or equivalent, Gardco Incorporated, Pompano Beach, Fla.) with a width of 10.2 cm to 15.2 cm and a gap of 0.05 mm is also heated. On a flat and level lab bench is placed a series of 10, 7.6 cm×20.3 cm polypropylene backsheet films, each with a basis weight of 18 gsm. These 10 backsheet films are separated by about 5 cm from one another and each is taped to the lab bench with transparent tape running across the top most edge of each film.

After taping the backsheet films to the lab bench, the hot wetness indicator composition is removed from the oven and placed in the vicinity of the top most edge of the backsheet film. The hot bird applicator is also removed from the oven and placed near the top most edge of the backsheet with its long dimension running parallel to the short 7.6 cm dimension of the backsheet film and its legs resting firmly on the lab bench rather than on the backsheet film itself. Next, the hot wetness indicator composition is dispensed along the front edge of the bird applicator and while firmly holding the left and right legs of the bird applicator with downward pressure, move the bird applicator in the direction of the long dimension of the backsheet film while maintaining the bird applicator's long dimension parallel to the short width dimension of the backsheet film.

The basis weight of the wetness indicators applied to the backsheet may be varied by changing the viscosity of the wetness indicator composition, by applying the composition at different temperatures, by changing the speed at which the bird applicator is dragged across the backsheet film, or by varying the gap of the bird applicator.

The basis weight of the wetness indicator composition applied to the backsheet film can be calculated by cutting out the wetness indicator of known dimensions and weighing it on a balance. The basis weight of the wetness indicator composition and backsheet film combination is calculated by dividing the mass of the backsheet film in units of grams by its area in units of square meters ($m^2$). To calculate the basis weight of the wetness indicator applied to the backsheet film, subtract the basis weight of the backsheet film from the basis weight calculated for the wetness indicator composition applied to the backsheet film.

After the wetness indicators are prepared and the basis weights calculated, they are applied to the dusting layer of a substantially cellulose free core by firmly pressing them onto the core with the wetness indicator side in direct contact with the dusting layer of the substantially cellulose free core. The wetness indicator is applied to the dusting layer using a metal roller having a radius of approximately 6 cm, a width of 5.5 cm, and a weight of 5 kg. After applying the wetness indicator film on top of the dusting layer of the core, the roller is rolled across the wetness indicator film 3 times along the long dimension of the film in a time of less than 5 seconds.

CTH room placement: After the wetness indicators have been applied to the dusting layer of the substantially cellulose free core, they are placed dusting layer side up in a controlled temperature and humidity room which is controlled to a humidity of 75%±5% and a temperature of 40° C.±2° C. The time and date at which the wetness indicators are placed in the room is recorded, and the samples are periodically checked for any color changing activity (e.g., a 5 days, 10 days, 20 days, 50 days, and/or 75 days). For bromocresol green containing compositions, such as Samples A-H, the initial and stable dry state color is yellow. Any color change observed for the wetness indicator compositions is quantified according to the following 6-point scale of 0 to 5. It is to be appreciated that the color changes may be observed and/or quantified by any suitable means known in the art such as, for example, digital photography.

"0" corresponds to no visible color change of the wetness indicator through the backsheet film (e.g., bromocresol green containing compositions remain completely yellow);

"1" corresponds to the presence of a color change over less than 10% of the backsheet film area corresponding to the wetness indicator area (i.e., green or blue regions for bromocresol green containing compositions);

"2" corresponds to the presence of a color change over 10% to 40% of the backsheet film area corresponding to the wetness indicator area;

"3" corresponds to the presence of a color change over 41% to 60% of the backsheet film area corresponding to the wetness indicator area;

"4" corresponds to the presence of a color change over 61% to 90% of the backsheet film area corresponding to the wetness indicator area; and "5" corresponds to the presence of a color change over greater than 90% of the backsheet film area corresponding to the wetness indicator area.

The wetness indicators are photographed or graded in this manner for storage in a controlled temperature and humidity rooms at the conditions described hereinabove.

B. Colorant Kinetics Test Method:

After the wetness indicators are made (they are in the form of a film) and applied to the substantially cellulose free cores as described above in the CTH stability test, the wetness indicators can be tested to determine how quickly they change from their stabilized dry state color to their wet state color after being contacted with synthetic urine. For wetness indicators with wetness indicator compositions containing only bromocresol green, the dry state color is yellow and the wet state color is blue. The wetness indicators applied to the dusting layer of the substantially cellulose free core should approximately mimic both the basis weight and dimensions of the wetness indicators that would be marketed to consumers. Thus, a basis weight of 20 gsm to 60 gsm would be most appropriate with dimensions of approximately 5 mm in width by 160 mm in length. This wetness indicator should be applied to the dusting layer such that is its long dimension is parallel to the long dimension of the diaper. And, it should also be applied on the outside face of the dusting layer such that it runs along the center of the core of the diaper.

First, the diaper comprising the wetness indicator is placed with the wetness indicator side down (topsheet side up) on a clear, transparent, and colorless piece of polycarbonate with dimensions of 35.6 cm long by 15.2 cm wide by 0.63 cm thick. This polycarbonate sheet is supported on both ends with legs. A mirror is positioned directly below the sample and angled at 45 degrees so the wetness indicator side of the diaper can be viewed during the colorant kinetics test.

Another clear, transparent, and colorless polycarbonate sheet is placed on the topsheet side of the diaper. A round hole of 3.81 cm in diameter is cut into this polycarbonate sheet with the center of the hole located in the middle of the 15.2 cm width dimension and 12.7 cm from one of the edges in the 35.6 cm long dimension. A 7.6 cm long, clear, transparent, polycarbonate cylinder is placed over the hole. The cylinder has an inner diameter of 3.81 cm and a wall thickness of 0.63 cm. The cylinder is placed over the 3.81 cm round hole in the polycarbonate sheet such that the inner periphery of the cylinder is substantially aligned with the periphery of the 3.81 cm hole in the polycarbonate sheet. After alignment is confirmed, the cylinder is glued permanently onto the sheet.

The top polycarbonate sheet is placed on top of the diaper so that the center of the polycarbonate cylinder sits on top of the core in a location selected to accept the initial urination event. After placing this polycarbonate sheet on the diaper, two 2 to 4 kg weights are placed on either end of the sheet in order to mimic the weight of a baby on top of the diaper.

Synthetic urine is prepared according to the recipe disclosed in U.S. Pat. No. 6,772,708 to Klofta. The synthetic urine is then heated to a temperature of 38° C. in order to mimic human body temperature. 40 milliliters of this heated synthetic urine is measured into a graduated cylinder. The 40 milliliters of heated synthetic urine is poured from the graduated cylinder into the polycarbonate cylinder on top of the diaper at a rate of approximately 2-3 milliliters per second. After all of synthetic urine is poured into the cylinder, a stop watch is started. An additional 40 milliliters is poured into the cylinder at a rate of approximately 2-3 milliliters per second at both the 5 and 10 minute time points as measured using the stop watch.

The color of the wetness indicator is observed and recorded (as can be seen through the backsheet) at 2 minutes and 5 minutes after the first 40 milliliter volume of synthetic urine is poured into the cylinder. After the second dose of 40 milliliters of synthetic urine is added at the 5 minute point, the color of the wetness indicator is recorded at the 10 minute point (i.e., 5 minutes after the second dose). After the third dose of 40 milliliters is added at the 10 minute point, the color of the wetness indicator is recorded at the 15 minute point (i.e., 5 minutes after the third dose). The color change can be measured using the following 6-point scale of 0 to 5:

0 denotes no color change of the wetness indicator through the backsheet film remaining in its dry state color, such that the wetness indicator remains completely yellow over the backsheet film area corresponding to the wetness indicator area;

1 denotes less than 10% of the backsheet film area corresponding to the wetness indicator area changing to the wet state color;

2 denotes 10-40% of the backsheet film area corresponding to the wetness indicator area changing to the wet state color;

3 denotes 41-60% of the backsheet film area corresponding to the wetness indicator area changing to the wet state color;

4 denotes 61-90% of the backsheet film area corresponding to the wetness indicator area changing to the wet state color; and 5 denotes greater than 90% of the backsheet film area corresponding to the wetness indicator area changing to the wet state color.

TABLE 1

| Component | A | B | C | D | E | F | G | H |
|---|---|---|---|---|---|---|---|---|
| Tackifier[1] | 33.00 | 33.01 | 32.76 | 32.95 | 32.61 | 34.40 | 58.8 | 48.8 |
| Tackifier[2] | 15.00 | 15.01 | 14.93 | 15.01 | 14.81 | 15.57 | | |
| HLB Modifier[3] | 19.03 | 18.99 | 19.06 | 19.03 | 18.96 | 19.42 | 16.0 | 16.0 |
| Stabilizer[4] | 3.41 | 3.41 | 3.17 | 2.95 | 2.85 | 2.08 | 5.0 | 9.0 |
| Stabilizer[5] | 0.20 | — | — | — | — | — | — | — |
| Water-soluble or water-dispersible chemical or polymer[6] | 1.00 | 1.00 | 1.13 | 0.81 | 0.99 | 1.04 | 1.0 | 1.0 |
| Water-soluble or water-dispersible chemical or polymer[7] | — | — | — | — | 1.95 | 2.01 | 3.0 | 3.0 |
| Colorant[8] | 0.18 | 0.18 | 0.20 | 0.20 | 0.20 | 0.20 | 0.20 | 0.2 |

TABLE 1-continued

| Component | A | B | C | D | E | F | G | H |
|---|---|---|---|---|---|---|---|---|
| Colorant[9] | — | — | — | 0.02 | — | — | — | — |
| Surfactant[10] | 27.78 | 28.01 | 28.44 | 28.52 | 27.37 | 24.98 | 12.0 | 18.0 |
| Anti-Oxidant[11] | 0.40 | 0.39 | 0.31 | 0.51 | 0.26 | 0.30 | 0.3 | 0.3 |
| CTH Stability Test (5 days) | 0 | 1 | 1 | 1 | 2 | 3 | 4 | 3 |
| Colorant Kinetics Test (at 5 minutes) | 4 | 4 | 4 | 4 | 4 | 4 | 3 | 3 |

[1]Pentaerythritol Rosin Ester, (SYLVATAC RE 98 from Arizona Chemical, Jacksonville, FL)
[2]Polymerized Rosin (SYLVAROS PR-295 from Arizona Chemical, Jacksonville, FL)
[3]W835 Microcrystalline Wax from Crompton, Petrolia, PA
[4]Cetyl Phosphate Free Acid (HOSTAPHAT CC-100 from Clariant)
[5]Anhydrous Citric Acid, (EMD)
[6]Cocoalkylmethyl[ethoxylated(15)] ammonium chloride (ETHOQUAD C/25) from Akzo Incorporated, Chicago, IL).
[7]Dimethyl(2-ethylhexylhydrogenated tallowalkyl) ammonium methyl sulfate, (HTL8(W)-MS from Akzo Incorporated, Chicago, IL)
[8]Bromocresol Green, Free Acid from Curtiss Labs, Bensalem, PA
[9]D&C Red #17 (Sensient Inc.)
[10]$C_{20}$-$C_{40}$ Pareth-10 (PERFORMATHOX 450 from New Phase Incorporated, Sugar Land, TX)
[11]IRGANOX 1010FF brand antioxidant from Ciba, Table 1 illustrates the results of the CTH Stability Test on several wetness indicator compositions. Each of the samples A-H are made by mixing the HLB modifier and viscosity modifier and heating the mixture at 100° C. until completely melted. Reduce the heat on this HLB/Viscosity modifier premix to 95° C. and maintain mixing. In another clean, glass container, mix the first binding agent, stabilizer, and the surfactant. Heat and stir this mixture at 90° C. until completely melted. Add in the HLB/Viscosity modifier premix to the mixture of first binding agent/stabilizer/surfactant and heat and mix at 90° C. Add to this mixture the second binding agent and mix until the temperature reaches 90° C. Finally, add to this mixture the colorant and mix for approximately 1 hour at 90° C. until the mixture is clear, transparent and light orange in color. The color change of Samples A-H illustrated in Table 1 is observed and recorded after 5 days in the CTH room (i.e., within 1 hour of the beginning of the sixth day of storage).

TABLE 2

| | Sample | | | | | |
|---|---|---|---|---|---|---|
| | H9219 | H9490 | H9567 | Pampers | Huggies | Unicharm |
| CTH Stability (at 10 days) | | | 0 | | | |
| CTH Stability (at 20 days) | | | 0 | | | |
| CTH Stability (at 50 days) | | | 0 | | | |
| CTH Stability (at 75 days) | | | 0 | | | |
| CTH Stability (at 90 days) | | | 0 | | | |

Table 2 illustrates the CTH Stability Test results of various commercially available wetness indicators. The Samples in the first three columns of Table 2 are commercially available wetness indicators sold under the product codes H9219, H9490, and H9567, respectively, by the Bostik, Corporation of Wauwatosa, Wis. The H9219 and H9490 samples are prepared according to the "handmade" procedure in the CTH Stability Test. The H9567 Sample is applied to the wearer facing side of the film layer of a disposable diaper backsheet during a commercial manufacturing process, and tested according to the "premade" procedure in the CTH Stability Test. The Sample identified as "Pampers" is a size 4 PAMPERS CRUSIERS brand disposable diaper, available from the Procter & Gamble Company of Cincinnati, Ohio. The Pampers sample includes a wetness indicator sold under the product code h9219, from Bostik, applied to the wearer facing side of the backsheet film layer. The Sample identified as "Huggies" is a size 4, HUGGIES brand disposable diaper, available from the Kimberly Clark Corporation of Neenah, Wis. The Sample identified as "Unicharm" is a size 4 UNICHARM brand disposable diaper, available from the Unicharm Corporation, Japan. The Huggies and Unicharm samples each include a wetness indicator applied to the wearer facing side of the backsheet film layer. The test samples shown in Table 2 are observed daily and any color change of the wetness indicator is recorded. Table 2 shows the color change of the samples recorded after 10, 20, 50, and 75 days in the CTH room. As can be seen in Table 2, the H9567 wetness indicator exhibits superior color stablility after 75 days.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
   an absorbent core and a backsheet, the backsheet including a film layer joined to a nonwoven layer;

a wetness indicator disposed on the film layer, the wetness indicator including a first acidic stabilizer, a second acidic stabilizer, a colorant, and a matrix, the matrix including a tackifier, a low molecular weight polyethylene glycol and a high molecular weight polyethylene glycol, and a water-dispersible polymer; and wherein the wetness indicator exhibits no visible color change through the backsheet film layer after 5 days according to the CTH Stability Test;

wherein the second acidic stabilizer is anhydrous citric acid; and wherein the anhydrous citric acid is present in a smaller amount than the first acidic stabilizer.

2. The absorbent article of claim 1, further comprising a dusting layer, the dusting layer being disposed between the backsheet and the absorbent core.

3. The absorbent article of claim 2, wherein the wetness indicator is disposed on a side of the film layer that faces the dusting layer.

4. The absorbent article of claim 2, wherein the dusting layer has a mean flow pore size greater than about 1 micron.

5. The absorbent article of claim 2, wherein the dusting layer has a hydrohead greater than about 1 mm of water.

6. The absorbent article of claim 2, wherein the dusting layer has a fiber diameter greater than about 10 nanometers.

7. The absorbent article of claim 1, wherein the colorant has a first color state associated with a first wetness indicator state and a second color state associated with a second wetness indicator state.

8. The absorbent article of claim 7, wherein the colorant is immobilized by the tackifier when the colorant is in the first color state and immobilized by at least one of the water-soluble polymer and water-dispersible polymer when the colorant is in its second color state.

9. The absorbent article of claim 7, wherein the first wetness indicator state is dry and the second wetness indicator state is wet.

10. The absorbent article of claim 1, wherein the colorant is a pH indicator.

11. The absorbent article of claim 1, wherein the colorant is selected from the group consisting of bromocresol green, bromocresol purple, bromophenol blue, m-cresol purple, cresol red, chlorophenol red, bromothymol blue, bromopyrogallol red, bromoxylenol blue, acridine, acridine orange, oil soluble dyes, pigments, and combinations thereof.

12. The absorbent article of claim 1, wherein the backsheet has a water vapor transmission rate greater than about 100 g/m$^2$/24 hrs.

13. The absorbent article of claim 1, wherein the backsheet has a basis weight greater than about 5 g/m$^2$.

14. The absorbent article of claim 1, wherein the wetness indicator is applied to the backsheet in one or more patterns selected from the group consisting of stripes, dots, geometric shapes, irregular shapes, alphanumeric characters, anthropomorphic images, pictorial representation of animals, pictorial representation of inanimate objects, cartoon characters, logos, trademarks and combinations thereof.

15. The absorbent article of claim 1, wherein the nonwoven layer is surfactant free.

16. An absorbent article comprising:
    an absorbent core including a complex of absorbent polymer material and thermoplastic adhesive material, the absorbent core being substantially cellulose free;
    a backsheet disposed on an outer facing surface of the absorbent article, the backsheet including a film layer joined to a second nonwoven layer; and
    a wetness indicator disposed on the film layer, the wetness indicator including a first acidic stabilizer, a second acidic stabilizer, a colorant, and a matrix, the matrix including a tackifier and at least one of a water-soluble polymer and a water-dispersible polymer;
    wherein the wetness indicator exhibits no visible color change through the backsheet film layer after 5 days according to the CTH Stability Test;
    wherein the second acidic stabilizer is anhydrous citric acid; and
    wherein the anhydrous citric acid is present in a smaller amount than the first acidic stabilizer.

17. The absorbent article of claim 16, wherein the colorant is immobilized by the tackifier when the colorant is in the first color state and immobilized by at least one of the water-soluble polymer and water-dispersible polymer when the colorant is in its second color state.

18. The absorbent article of claim 17, wherein the first wetness indicator state is dry and the second wetness indicator state is wet.

19. The absorbent article of claim 16, wherein the wetness indicator exhibits a color change within 15 minutes of being contacted with liquid, according to the Color Kinetics Test.

* * * * *